United States Patent [19]

Thornton

[11] 4,277,297

[45] Jul. 7, 1981

[54] METHOD OF FORMING DENTAL FLOSS WITH STRING AND BRUSH PORTIONS

[75] Inventor: Thomas F. Thornton, New Canaan, Conn.

[73] Assignee: Educational Health Products, Inc., New Canaan, Conn.

[21] Appl. No.: 102,797

[22] Filed: Dec. 12, 1979

Related U.S. Application Data

[60] Division of Ser. No. 599,485, Jul. 28, 1975, abandoned, which is a continuation-in-part of Ser. No. 138,501, Aug. 27, 1971, abandoned, and Ser. No. 361,237, May 17, 1973, Pat. No. 3,896,824.

[51] Int. Cl.³ .................. D02G 3/34; A61C 15/00
[52] U.S. Cl. .................................. 156/161; 28/252; 132/93; 156/180; 428/399
[58] Field of Search ............ 132/89, 93; 156/180, 156/161, 441; 28/252, 253, 243, 229; 57/295, 108, 297, 246; 427/175, 390; 428/399, 400, 375

[56] References Cited

U.S. PATENT DOCUMENTS

| | | | |
|---|---|---|---|
| 1,069,874 | 8/1913 | Hanscom | 132/93 |
| 2,878,548 | 3/1959 | Lohr et al. | 428/399 |
| 3,103,098 | 9/1963 | Dyer | 428/400 |
| 3,129,485 | 4/1964 | Shattuck | 28/253 |
| 3,284,871 | 11/1966 | Yano et al. | 28/253 |
| 3,930,059 | 12/1975 | Wells | 132/93 |

FOREIGN PATENT DOCUMENTS

841686 of 1960 United Kingdom .

Primary Examiner—Michael W. Ball

[57] ABSTRACT

A teeth cleaner to be passed through a crevice between adjacent teeth for dislodging particles therein consisting of a plurality of elongate filaments having a string portion in which the filaments are parallel and closely packed and a spongy brush portion of larger diameter caused by the textured filaments being randomly distorted and a yarn formed therefor.

5 Claims, 3 Drawing Figures

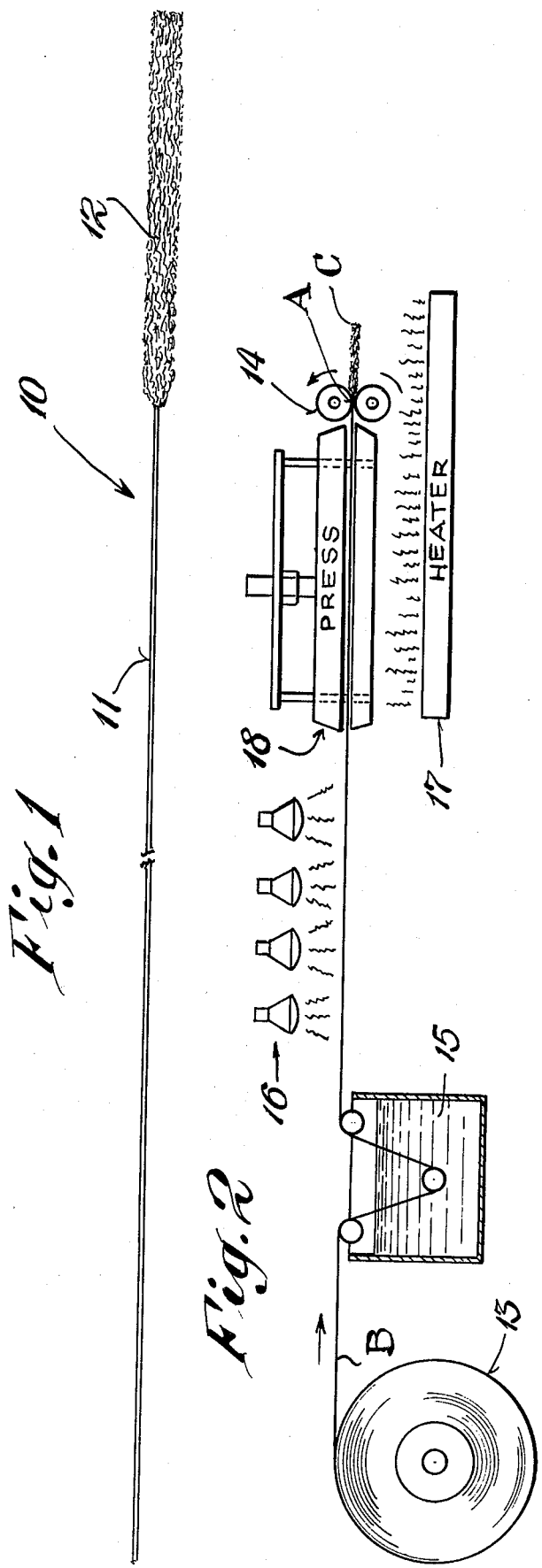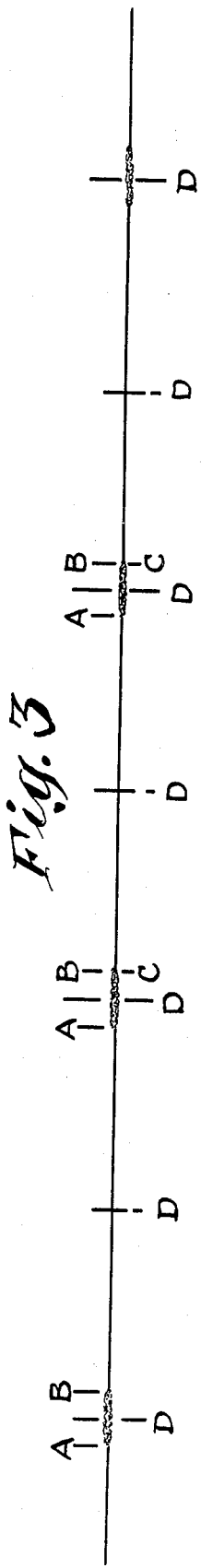

METHOD OF FORMING DENTAL FLOSS WITH STRING AND BRUSH PORTIONS

This is a division of application Ser. No. 599,485, filed July 28, 1975, now adandoned, which is a continuation-in-part of my applications, Ser. No. 138,501, filed Aug. 27, 1971, now abandoned, and entitled Teeth Cleaning, and Ser. No. 361,237, filed May 17, 1973 and now U.S. Pat. No. 3,896,824.

In dental hygiene, it has been found desirable to remove particles of food that may be trapped in the crevices between adjacent teeth. It is well known to use a length of string, commonly called dental floss, to physically remove these particles by passing the string through the crevice. The string is essentially of a small constant diameter and is normally incapable of filling the crevice to resiliently engage the surfaces of the teeth defining the crevice. Thus, while the string or floss removes some particles, there is no assurance that it will essentially completely fill the crevice to physically and mechanically remove all the particles in the crevice and to rub against and abrase the surfaces of the teeth defining the cavity.

It is an object of the present invention to provide a teeth cleaner which is capable of being as easily inserted into a crevice between teeth as dental floss but yet which is capable of essentially completely filling the crevices to assure complete removal of particles therein.

Another object of the present invention is to provide a teeth cleaner which has a portion which is formed to be of a diameter normally larger than the crevice but yet in which the spongy portion is resiliently compressible to enable it to adapt to the shape of the crevice.

A further object of the present invention is to achieve the above objects with a teeth cleaner that is economical to manufacture and does not deteriorate with only a single use so that it may be used for numerous crevices.

In carrying out the present invention, the teeth cleaner herein specifically described consists of a plurality of elongate filaments or fibers that extend throughout the length of the cleaner. One portion of the filaments are formed to be a string portion by being essentially parallel and closely packed so that they in effect resemble conventional dental floss. The remaining portion of the filaments form a brush portion with the filaments extending in the same direction as in the string portion but by being textured, i.e. randomly crinkled and commingled, the brush portion is thus spongy and of a larger thickness than the string portion. It is thus essentially elastic, capable of being easily reduced in diameter by a compression force or an elongating force but yet having memory which causes them to return to their normal bulky or crinkled state upon removal of the thickness reducing force.

Other features and advantages will hereinafter appear.

In the drawing:

FIG. 1 is a view of the teeth cleaner of the present invention.

FIG. 2 is a diagrammatic view of one method of forming teeth cleaners.

FIG. 3 shows the manner of forming individual cleaners from the continuous length produced by the method shown in FIG. 2.

Referring to the drawing, the teeth cleaner of the present invention is generally indicated by the reference numeral 10 and includes a string portion 11 and a brush portion 12. The cleaner 10 may be formed by the apparatus shown in FIG. 2 by unwinding a length of six hundred denier textured nylon yarn from a spool 13 under tension produced by rollers 14 so that the yarn, between the point A at the rollers and the point B at the spool, is under a tension of 1 to 10 pounds. The tensioned yarn is guided through a bath 15 of nylon resin dissolved in alcohol and then partially dried for thirty seconds by heat lamps 16. The yarn is then subjected to heat by a heater 17 for complete drying and pressure from a press 18. A portion of the yarn from the point A to the point C is not placed under tension while it is being dried.

The yarn is continually processed to produce a continuous length of teeth cleaner shown in FIG. 3. The points A and C are indicated where they will occur and it will be seen that basically the points B and C correspond. The continuous yarn is then severed at each of the points D to produce the individual cleaners 10.

It will be understood that the textured yarn on the spool 13 consists of perhaps 200 to 300 continuous filaments that were parallel and smooth but which have been textured by mechanical and/or heat treatments to permanently set or form coils, curves, twists, crimps and/or loops in the parallel filaments. Such yarn is generally commercially available with one or more filaments and may be of the type disclosed in U.S. Pat. Nos. 2,919,524; 3,077,724 and 3,091,912, though, of course, the invention is not to be limited thereto but includes textured and/or bulk, stretch yarns that have coiled, curled, crumped or loop distorted and commingled filaments.

The stretching of the yarn between the points A and B causes the yarn to stretch and remove the set coils, crimp and/or loops so that the yarn that forms the string portion 11 has its filaments become straight and parallel. The nylon resin from the bath coats the filaments and thus prevents them from becoming textured again upon release of the tension. The brush portion 12 is completely dried while under no tension so that it reverts to becoming textured again. Moreover, the nylon resin also coats the bulky brush portion to somewhat stiffen it and to give it more resistance to being compressed.

In use, the string portion effectively acts as dental floss, permitting easy insertion past the contact point of the crowns of adjacent teeth into the crevice between the teeth with the dislodgment of particles at the contact points. The string portion is then pulled, to cause the brush portion to enter into and pass through the crevice. The brush portion rubs against the sides of the teeth to be compressed to assume the shape of the crevice and as it is pulled through it dislodges particles therein between the gum line and the contact points. The brush portion then after removal reverts to its initial noncompressed bulky shape to permit it to be used in the next crevice.

It will be understood that the brush portion is thus a spongy mass of textured nylon filaments which are held together with the nylon resin to be elastic, spongy and have memory.

While the above description of the teeth cleaner presupposes that each cleaner will be individual as supplied to a user, it is also contemplated that the teeth cleaners may be packaged as a continuous strand, such as shown in FIG. 3 prior to severing, so that the cleaners are joined to each other with the user severing each cleaner from the length as is desired.

On the other hand, if desired the lengths of yarn having alternate string and brush portions may be left unsevered, and be used in the manufacture of fabrics. Thus, the present invention while specifically mentioning the use of the processed yarn as a tooth cleaner is not to be considered as preventing its use in woven or knitted fabrics.

Variations and modifications may be made within the scope of the claims and portions of the improvements may be used without others.

I claim:

1. Method of producing a continuous length of multi-diameter, multi-filament yarn having alternate string portions comprising straight, parallel, closely packed filaments and compressible, spongy brush portions comprising crinkled filaments which are stiffened to render them more resistant to compression, comprising the steps of producing a continuous length of yarn comprising a plurality of textured, commingled filaments that have been permanently crinkled, coating said yarn with a hardenable resin coating, stretching said coated alternate string portions to straighten the filaments therein and render them parallel to each other and closely packed while retaining said brush portions in a relaxed, crimped condition, heating said coated yarn to harden said resinous coating and render the filaments in said alternate string lengths essentially straight and crinkle resistant and to render the filaments in said brush portions stiffened and more resistant to compression, and relaxing said stretch on said string portions to form said continuous length comprising said alternate straight string portions and said stiffened, crinkled brush portions, said brush portions comprising lengths of said yarn which have not been rendered straight and crinkle resistant and in which the filaments are crinkled, to render the diameter of said brush portions larger than the diameter of said string portions, and are coated with resin and stiffened to render them more resistant to compression.

2. Method according to claim 1 in which said yarn comprises between about 200 and 300 filaments.

3. Method according to claim 1 in which said filaments comprise nylon filaments.

4. Method according to claim 1 in which said resin coating comprises nylon resin dissolved in a volatile solvent.

5. Method according to claim 1 in which said coated yarn is initially heated to dry the resin coating and then said string portions are heated and pressed to render said string portions straight and crinkle resistant.

* * * * *